(12) United States Patent
Avory et al.

(10) Patent No.: US 8,940,274 B2
(45) Date of Patent: Jan. 27, 2015

(54) RADIOIODINATION METHOD

(75) Inventors: Michelle Avory, Wendover (GB); Harry John Wadsworth, Bishops Stortford (GB); Robert James Domett Nairne, Amersham (GB)

(73) Assignee: GE Healthcare Limited, Amersham, Buckinghamshire (GB)

( * ) Notice: Subject to any disclaimer, the term of this patent is extended or adjusted under 35 U.S.C. 154(b) by 92 days.

(21) Appl. No.: 13/988,880

(22) PCT Filed: Nov. 23, 2011

(86) PCT No.: PCT/EP2011/070808
§ 371 (c)(1),
(2), (4) Date: Aug. 6, 2013

(87) PCT Pub. No.: WO2012/069535
PCT Pub. Date: May 31, 2012

(65) Prior Publication Data
US 2013/0315824 A1    Nov. 28, 2013

Related U.S. Application Data

(60) Provisional application No. 61/416,361, filed on Nov. 23, 2010.

(30) Foreign Application Priority Data

Nov. 23, 2010   (GB) .................................. 1019824.0

(51) Int. Cl.
| | | |
|---|---|---|
| A61K 51/08 | (2006.01) | |
| C07B 59/00 | (2006.01) | |
| A61K 51/04 | (2006.01) | |
| C07D 249/06 | (2006.01) | |
| C07D 261/08 | (2006.01) | |

(52) U.S. Cl.
CPC ............ *C07B 59/008* (2013.01); *A61K 51/0453* (2013.01); *C07B 59/002* (2013.01); *C07D 249/06* (2013.01); *C07D 261/08* (2013.01); *A61K 51/08* (2013.01)

USPC ....... 424/1.69; 424/1.11; 424/1.65; 424/1.85; 424/1.89

(58) Field of Classification Search
USPC .................... 424/1.11, 1.65, 1.69, 1.85, 1.89; 530/345
See application file for complete search history.

(56) References Cited

U.S. PATENT DOCUMENTS 7,041,859 B1    5/2006   Kabalka

FOREIGN PATENT DOCUMENTS

| WO | 98/18499 | 5/1998 |
|---|---|---|
| WO | 2006/067376 | 6/2006 |
| WO | 2006/116629 | 11/2006 |
| WO | 2007/148089 | 12/2007 |
| WO | 2009/011880 | 1/2009 |
| WO | 2009/020616 | 2/2009 |
| WO | 2010/037225 | 4/2010 |
| WO | 2011/020907 | 2/2011 |
| WO | 98/57809 | 5/2013 |

OTHER PUBLICATIONS

Ito, et al. Bioorganic & Medicinal Chemistry, 2008, vol. 16(22) pp. 9817-9829.
Chan, et al. Bioorganic & Medicinal Chemistry 2002, 10(9), pp. 3001-3010.
Eersels, et al. J. Lab.Comp.Radiopharm, vol. 48, 2005 pp. 241-257.
Ali, et al. Synthesis, George Thiem Verlag, Stuttgart, DE, 1996, pp. 423-445.
Kabalka, et al. Journal of Labelled Compounds and Radiopharmaceuticals, vol. 48, No. 5, Apr. 1, 2005 pp. 359-362.
Kabalka, et al. Journal of Labelled Compounds and Radiopharmaceuticals, vol. 50, No. 5-6, Apr. 1, 2007 pp. 446-447.
PCT/EP2011/070808 ISRWO.
GB 1019824.0 Search Report Dated Feb. 14, 2011.

*Primary Examiner* — Michael G. Hartley
*Assistant Examiner* — Jagadishwar Samala

(57) ABSTRACT

The present invention provides a novel method of labelling biological targeting molecules (BTMs) of interest with radioiodine. Also provided are functionalised BTMs useful in the method, as well as methods of preparing such functionalised BTMs under mild conditions.

11 Claims, No Drawings

RADIOIODINATION METHOD

This application is a filing under 35 U.S.C. 371 of international application number PCT/EP2011/070808, filed Nov. 23, 2011 which claims priority to U.S. application No. 61/416,361 filed Nov. 23, 2010 and Great Britain application number 1019824.0 filed Nov. 23, 2010, in the entire disclosure of which is hereby incorporated by reference.

FIELD OF THE INVENTION

The present invention provides a novel method of labelling biological targeting molecules (BTMs) of interest with radioiodine. Also provided are functionalised BTMs useful in the method, as well as methods of preparing such functionalised BTMs under mild conditions.

BACKGROUND TO THE INVENTION

Methods of incorporating radiohalogens into organic molecules are known [Bolton, J. Lab. Comp. Radiopharm., 45, 485-528 (2002)]. For the case of $^{123}$I-labelled radiopharmaceuticals, Eersels et at [J. Lab. Comp. Radiopharm., 48, 241-257 (2005)] have compared the 4 principal synthetic routes:
  (i) oxidative radioiodination;
  (ii) nucleophilic isotopic exchange;
  (iii) nucleophilic non-isotopic exchange;
  (iv) electrophilic labelling.

Route (iv) typically involves the use of an organometallic precursors, such as trialkyltin, trialkylsilyl or organomercury or organothallium derivative. Of these, the radioiododestannylation route was acknowledged as having become the preferred electrophilic labelling method, due to the possibility of regiospecific radioiodination at room temperature. Eersels et al concluded, however, that there was no overall preferred radioiodination method, since the choice depends on the nature of the compound to be radioiodinated.

The use of organotin intermediates in radiopharmaceutical synthesis has been reviewed by Ali et al [Synthesis, 423-445 (1996)]. Kabalka et al have published extensively on the use of organoborane precursors to permit radioisotope and radiohalogen labelling [see eg. J. Lab. Comp. Radiopharm., 50, 446-447 and 888-894 (2007)].

The applications of "click chemistry" in biomedical research, including radiochemistry, have been reviewed by Nwe et al [Cancer Biother. Radiopharm., 24(3), 289-302 (2009)]. As noted therein, the main interest has been in the PET radioisotope $^{18}$F (and to a lesser extent $^{11}$C), plus "click to chelate" approaches for radiometals suitable for SPECT imaging such as $^{99m}$Tc or $^{111}$In. $^{18}$F click-labelling of targeting peptides, giving products incorporating an $^{18}$F-fluoroalkyl-substituted triazole have been reported by Li et al [Bioconj. Chem., 18(6), 1987-1994 (2007)], and Hausner et al [J. Med. Chem., 51(19), 5901-5904 (2008)].

WO 2006/067376 discloses a method for labelling a vector comprising reaction of a compound of formula (I) with a compound of formula (II):

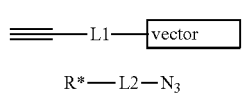

or,
a compound of formula (III) with a compound of formula (IV)

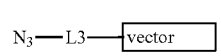
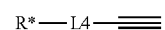

in the presence of a Cu(I) catalyst, wherein:
  L1, L2, L3, and L4 are each Linker groups;
  R* is a reporter moiety which comprises a radionuclide;
to give a conjugate of formula (V) or (VI) respectively:

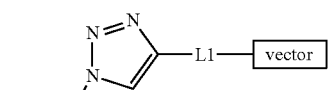

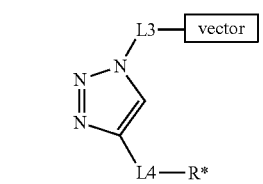

wherein L1, L2, L3, L4, and R* are as defined above.

R* of WO 2006/067376 is a reporter moiety which comprises a radionuclide for example a positron-emitting radionuclide. Suitable positron-emitting radionuclides for this purpose are said to include $^{11}$C, $^{18}$F, $^{75}$Br, $^{76}$Br, $^{124}$I, $^{82}$Rb, $^{68}$Ga, $^{64}$Cu and $^{62}$Cu, of which $^{11}$C and $^{18}$F are preferred. Other useful radionuclides are stated to include $^{123}$I, $^{125}$I, $^{131}$I, $^{211}$At, $^{99m}$Tc, and $^{111}$In.

WO 2007/148089 discloses a method for radiolabelling a vector comprising reaction of a compound of formula (I) with a compound of formula (II):

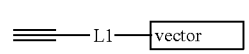

or, a compound of formula (III) with a compound of formula (IV):

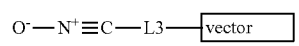
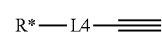

in the presence of a Cu(I) catalyst, wherein:
  L1, L2, L3, and L4 are each Linker groups;
  R* is a reporter moiety which comprises a radionuclide;
to give a conjugate of formula (V) or (VI) respectively:

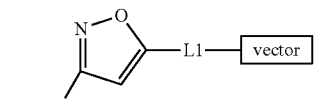

-continued

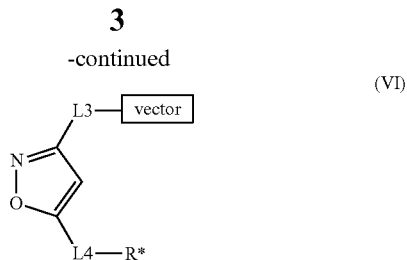
(VI)

In both WO 2006/067376 and WO 2007/148089, metallic radionuclides are stated to be suitably incorporated into a chelating agent, for example by direct incorporation by methods known to the person skilled in the art.

WO 2006/116629 (Siemens Medical Solutions USA, Inc.) discloses a method of preparation of a radiolabelled ligand or substrate having affinity for a target biomacromolecule, the method comprising:
(a) reacting a first compound comprising
  (i) a first molecular structure;
  (ii) a leaving group;
  (iii) a first functional group capable of participating in a click chemistry reaction; and optionally,
  (iv) a linker between the first functional group and the molecular structure, with a radioactive reagent under conditions sufficient to displace the leaving group with a radioactive component of the radioactive reagent to form a first radioactive compound;
(b) providing a second compound comprising
  (i) a second molecular structure;
  (ii) a second complementary functional group capable of participating in a click chemistry reaction with the first functional group, wherein the second compound optionally comprises a linker between the second compound and the second functional group;
(c) reacting the first functional group of the first radioactive compound with the complementary functional group of the second compound via a click chemistry reaction to form the radioactive ligand or substrate; and
(d) isolating the radioactive ligand or substrate.

WO 2006/116629 teaches that the method therein is suitable for use with the radioisotopes: $^{124}I$, $^{18}F$, $^{11}C$, $^{13}N$ and $^{15}O$ with preferred radioisotopes being: $^{18}F$, $^{11}C$, $^{123}I$, $^{124}I$, $^{127}I$, $^{131}I$, $^{76}Br$, $^{64}Cu$, $^{99m}Tc$, $^{90}Y$, $^{67}Ga$, $^{51}Cr$, $^{192}Ir$, $^{99}Mo$, $^{153}Sm$ and $^{201}Tl$. WO 2006/116629 teaches that other radioisotopes that may be employed include: $^{72}As$, $^{74}As$, $^{75}Br$, $^{55}Co$, $^{61}Cu$, $^{67}Cu$, $^{68}Ga$, $^{68}Ge$, $^{125}I$, $^{132}I$, $^{111}In$, $^{52}Mn$, $^{203}Pb$ and $^{97}Ru$. WO 2006/116629 does not, however, provide any specific teaching on how to apply the method to the radioiodination of biological molecules.

There is therefore still a need for alternative radioiodination methods.

The Present Invention

The present invention provides methodology for the radioiodination of biological targeting molecules (BTMs). The method has the advantage that it can be carried out under mild conditions, and is hence compatible with a range of biological molecules. The method uses functionalised BTMs, whereby a reactive functional group (Q in Formulae Ia and Ib) is introduced, so that site-specific radioiodination is achieved, with minimal non-specific radioiodination of the BTM.

The method uses precursors and functionalised BTMs which are non-radioactive, so that the radioiodine is introduced at the latest possible stage. This has the advantage that the non-radioactive chemicals can readily be purified to a high degree of purity, without the complication of radiation dose. The number of steps involving radioactivity is thus minimised, with consequent advantages of minimising radiation dose to the operator, minimising the risk of contamination ands minimising the loss of radioactive yield due to the radioactive decay during the preparative chemistry. The radiochemistry involves a single, straightforward and high-yielding step.

The method provides products in which the radioiodine is directly bonded to an triazole or isoxazole heteroaryl ring. The radioiodinated products are thus expected to exhibit good stability with respect to metabolic deiodination in vivo, with consequent unwanted stomach and/or thyroid uptake of radioiodine. The products are therefore suitable for use as radiopharmaceuticals for in vivo imaging, which is an important advantage.

The radioiodination methodology is readily adaptable to use with an automated synthesizer apparatus.

DETAILED DESCRIPTION OF THE INVENTION

In a first aspect, the present invention provides a method of radioiodination of a biological targeting moiety, said method comprising:
(i) provision of a functionalised BTM of Formula (Ia) or (Ib):

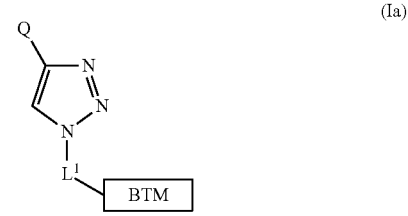
(Ia)

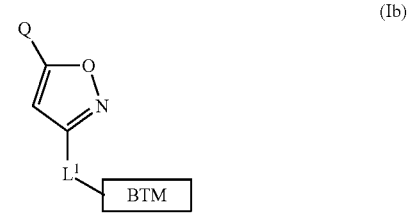
(Ib)

(ii) reaction of the functionalised BTM of either Formula (Ia) or (Ib) with radioactive iodide ion in the presence of an oxidising agent, to give the desired radioiodinated product as a conjugate of Formula (IIa) or (IIb) respectively;

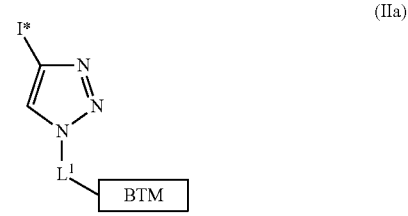
(IIa)

-continued

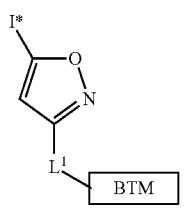

(IIb)

wherein:
BTM is the biological targeting moiety;
$L^1$ is a linker group which may be present or absent;
Q is $R^a{}_3Sn$— or $KF_3B$—, where each $R^a$ is independently $C_{1-4}$ alkyl;
I* is a radioisotope of iodine.

The term "radioiodination" has its conventional meaning, i.e. a radiolabelling process wherein the radioisotope used for the radiolabelling is a radioisotope of iodine.

When the linker group is absent, that means that the triazole rings of Formula (Ia) or (IIa), or the isoxazole rings of Formulae (IIa) or (IVa) respectively, are bonded directly to the BTM.

By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning.

The term radioisotope of iodine has its conventional meaning, i.e. an isotope of the element iodine that is radioactive. Suitable such radioisotopes include: $^{123}I$, $^{124}I$, $^{125}I$ and $^{131}I$. When the BTM is labelled with $^{131}I$, the product may be useful as a radiopharmaceutical for therapeutic applications in vivo, such as radioimmunotherapy when the BTM is an antibody or antibody fragment.

When Q is $KF_3B$—, that corresponds to a potassium trifluoroborate derivative as described below.

By the term "oxidising agent" is meant an oxidant capable of oxidising iodide ion to form the electrophilic species (HOI, $H_2OI$), wherein the active iodinating agent is $I^+$. Suitable oxidising agents are described by Bolton [J. Lab. Comp. Radiopharm., 45, 485-528 (2002)], and Eersels et at [J. Lab. Comp. Radiopharm., 48, 241-257 (2005)] and include peracetic acid and N-chloro compounds, such as chloramine-T, iodogen, iodogen tubes and succinimides. Preferred oxidising agents are peracetic acid (which is commercially available) at pH ca. 4, and hydrogen peroxide/aqueous HCl at pH ca. 1. Iodogen tubes are commercially available from Thermo Scientific Pierce Protein Research Products.

If the BTM or any residues therein are potentially sensitive to oxidation, it is possible to minimise the risk of oxidation of the BTM by controlling the order and amount of the reagents added to the radioiodinating reaction mixture. Thus, by using the minimum amount of oxidant and only adding the Compound of Formula (Ia) or (Ib) derivative when all the iodide has already been oxidised to $I^+$, unwanted oxidation of the BTM will be minimised. When Q is $R^a{}_3Sn$—, the kinetics of reaction between $I^+$ and the aryl stannane derivative are particularly fast, so unwanted oxidation of the BTM is likely to be a minor problem. An alternative solution is to use iodogen tubes so that the BTM does not come into contact with the oxidising species.

Preferred Aspects.

A preferred precursor for use in the method of the first aspect is the triazole of Formula (Ia), and hence a preferred product is the triazole of Formula (IIa). One reason is that the isonitrile oxides are typically less stable than azides. Consequently, whilst the azide of Formula (Ia) can be isolated and purified, the isonitrile oxide of Formula (Ib) will typically need to be generated in situ.

In the first aspect, Q is preferably $R^a{}_3Sn$. Preferred $R^a{}_3Sn$— groups are $Bu_3Sn$— or $Me_3Sn$—, preferably $Me_3Sn$—.

Preferred radioisotopes of iodine for use in the present invention are those suitable for medical imaging in vivo using PET or SPECT, preferably $^{123}I$, $^{124}I$ or $^{131}I$, more preferably $^{123}I$ (for SPECT) or $^{124}I$ (for PET), most preferably $^{123}I$.

The BTM may be of synthetic or natural origin, but is preferably synthetic. The term "synthetic" has its conventional meaning, i.e. man-made as opposed to being isolated from natural sources eg. from the mammalian body. Such compounds have the advantage that their manufacture and impurity profile can be fully controlled. Monoclonal antibodies and fragments thereof of natural origin are therefore outside the scope of the term 'synthetic' as used herein. The molecular weight of the BTM is preferably up to 30,000 Daltons. More preferably, the molecular weight is in the range 200 to 20,000 Daltons, most preferably 300 to 18,000 Daltons, with 400 to 16,000 Daltons being especially preferred. When the BTM is a non-peptide, the molecular weight of the BTM is preferably up to 3,000 Daltons, more preferably 200 to 2,500 Daltons, most preferably 300 to 2,000 Daltons, with 400 to 1,500 Daltons being especially preferred.

The biological targeting moiety preferably comprises: a 3-100 mer peptide, peptide analogue, peptoid or peptide mimetic which may be a linear or cyclic peptide or combination thereof; a single amino acid; an enzyme substrate, enzyme antagonist enzyme agonist (including partial agonist) or enzyme inhibitor; receptor-binding compound (including a receptor substrate, antagonist, agonist or substrate); oligonucleotides, or oligo-DNA or oligo-RNA fragments. The enzyme and/or receptor is preferably endogenous to the mammalian subject.

By the term "peptide" is meant a compound comprising two or more amino acids, as defined below, linked by a peptide bond (ie. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. The term "peptide analogue" refers to peptides comprising one or more amino acid analogues, as described below. See also *Synthesis of Peptides and Peptidomimetics*, M. Goodman et al, Houben-Weyl E22c, Thieme.

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)]. Radiolabelled amino acids such as tyrosine, histidine or proline are known to be useful in vivo imaging agents.

When the BTM is an enzyme substrate, enzyme antagonist, enzyme agonist, enzyme inhibitor or receptor-binding compound it is preferably a non-peptide, and more preferably is synthetic. By the term "non-peptide" is meant a compound which does not comprise any peptide bonds, ie. an amide bond between two amino acid residues. Suitable enzyme substrates, antagonists, agonists or inhibitors include glucose and glucose analogues; fatty acids, or elastase, Angiotensin II or metalloproteinase inhibitors. The enzyme of the enzyme substrate, antagonist, agonist or inhibitor is preferably endogenous to the mammalian subject. Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor. The receptor of the receptor-binding compound is preferably endogenous to the mammalian subject.

The BTM is most preferably a 3-100 mer peptide or peptide analogue. When the BTM is a peptide, it is preferably a 4-30 mer peptide, and most preferably a 5 to 28-mer peptide.

When the BTM is an enzyme substrate, enzyme antagonist, enzyme agonist or enzyme inhibitor, preferred such biological targeting molecules of the present invention are synthetic, drug-like small molecules i.e. pharmaceutical molecules. Preferred dopamine transporter ligands such as tropanes; fatty acids; dopamine D-2 receptor ligands; benzamides; amphetamines; benzylguanidines, iomazenil, benzofuran (IBF) or hippuric acid. Preferred tropane derivatives are $^{123}$I-CIT (Dopascan™) $^{123}$I-CIT-FP (DaTSCAN™) and the E isomer of $^{123}$I-2β-carbomethoxy-3β-(4-fluorophenyl)-N-(1-iodoprop-1-en-3-yl)nortropane (Altropane™). Dopascan™ and DaTSCAN™ are especially preferred. These and other tropane agents are described by Morgan and Nowotnik [Drug News Perspect., 12(3), 137-145 (1999). Preferred fatty acids are $^{123}$I-BMIPP and $^{123}$I-IPPA. Preferred amphetamine derivatives are $^{123}$I-IMP. A preferred benzylguanidine is meta-iodobenzylguanidine (MIBG), ie. $^{123}$I-MIBG.

When the BTM is a peptide, preferred such peptides include:
somatostatin, octreotide and analogues,
peptides which bind to the ST receptor, where ST refers to the heat-stable toxin produced by *E. coli* and other micro-organisms;
bombesin;
vasoactive intestinal peptide;
neurotensin;
laminin fragments eg. YIGSR, PDSGR, IKVAV, LRE and KCQAGTFALRGDPQG,
N-formyl chemotactic peptides for targeting sites of leucocyte accumulation,
Platelet factor 4 (PF4) and fragments thereof,
RGD (Arg-Gly-Asp)-containing peptides, which may eg. target angiogenesis [R. Pasqualini et al., Nat Biotechnol. 1997 June; 15(6):542-6]; [E. Ruoslahti, Kidney Int. 1997 May; 51(5):1413-7].
peptide fragments of $α_2$-antiplasmin, fibronectin or beta-casein, fibrinogen or thrombospondin. The amino acid sequences of $α_2$-antiplasmin, fibronectin, beta-casein, fibrinogen and thrombospondin can be found in the following references: $α_2$-antiplasmin precursor [M. Tone et al., J. Biochem., 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);
peptides which are substrates or inhibitors of angiotensin, such as: angiotensin II Asp-Arg-Val-Tyr-Ile-His-Pro-Phe (E. C. Jorgensen et al, *J. Med. Chem.*, 1979, Vol 22, 9, 1038-1044)
[Sar, Ile] Angiotensin II: Sar-Arg-Val-Tyr-Ile-His-Pro-Ile (R. K. Turker et al., *Science*, 1972, 177, 1203).
Angiotensin I: Asp-Arg-Val-Tyr-Ile-His-Pro-Phe-His-Leu.
Preferred BTM peptides are RGD peptides. A more preferred such RGD peptide comprises the fragment:

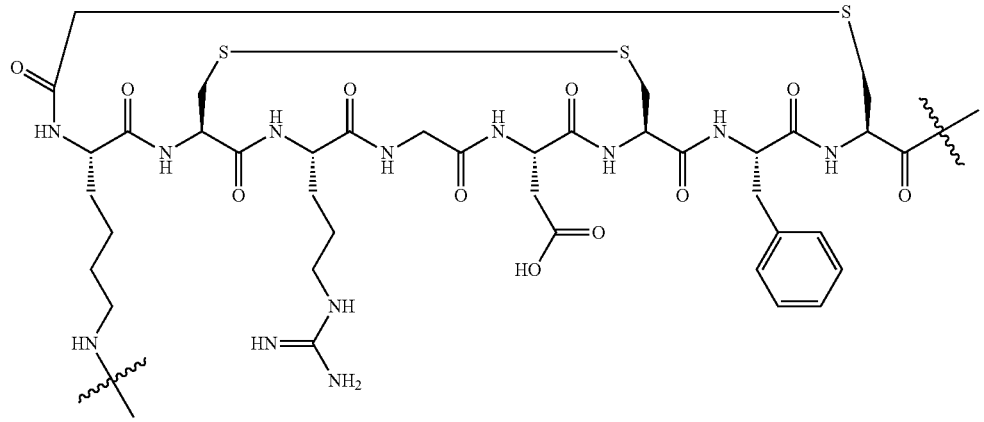 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

A most preferred such RGD peptide is when the BTM is a peptide of formula (A):

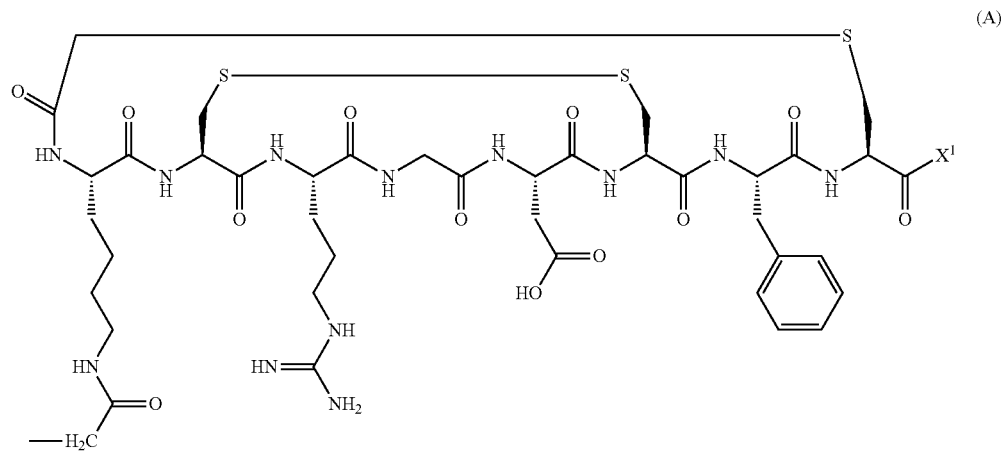

wherein $X^1$ is either —$NH_2$ or

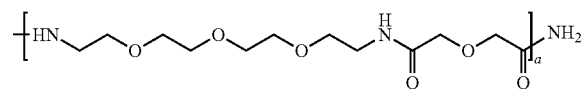

wherein a is an integer of from 1 to 10.

In Formula A, a is preferably 1.

When the BTM is a peptide, one or both termini of the peptide, preferably both, have conjugated thereto a metabolism inhibiting group ($M^{IG}$). Having both peptide termini protected in this way is important for in vivo imaging applications, since otherwise rapid metabolism would be expected with consequent loss of selective binding affinity for the BTM peptide. By the term "metabolism inhibiting group" ($M^{IG}$) is meant a biocompatible group which inhibits or suppresses enzyme, especially peptidase such as carboxypeptidase, metabolism of the BTM peptide at either the amino terminus or carboxy terminus. Such groups are particularly important for in vivo applications, and are well known to those skilled in the art and are suitably chosen from, for the peptide amine terminus:

N-acylated groups —NH(C=O)$R^G$ where the acyl group —(C=O)$R^G$ has $R^G$ chosen from: $C_{1-6}$ alkyl, $C_{3-10}$ aryl groups or comprises a polyethyleneglycol (PEG) building block. Suitable PEG groups are described for the linker group ($L^1$), below. Preferred such PEG groups are the biomodifiers of Formulae Bio1 or Bio2 (below). Preferred such amino terminus $M^{IG}$ groups are acetyl, benzyloxycarbonyl or trifluoroacetyl, most preferably acetyl.

Suitable metabolism inhibiting groups for the peptide carboxyl terminus include: carboxamide, tert-butyl ester, benzyl ester, cyclohexyl ester, amino alcohol or a polyethyleneglycol (PEG) building block. A suitable $M^{IG}$ group for the carboxy terminal amino acid residue of the BTM peptide is where the terminal amine of the amino acid residue is N-alkylated with a $C_{1-4}$ alkyl group, preferably a methyl group. Preferred such $M^{IG}$ groups are carboxamide or PEG, most preferred such groups are carboxamide.

In the method of the first aspect, a linker group ($L^1$) is preferably present. Preferred linker groups ($L^1$) are synthetic, and comprise a group of formula -$(A)_m$- wherein each A is independently —$CR_2$—, —CR=CR—, —C≡C—, —$CR_2CO_2$—, —$CO_2CR_2$—, —NRCO—, —CONR—, —NR(C=O)NR—, —NR(C=S)NR—, —$SO_2$NR—, —$NRSO_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block;

wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;

and m is an integer of value 1 to 20.

When $L^1$ comprises a peptide chain of 1 to 10 amino acid residues, the amino acid residues are preferably chosen from glycine, lysine, arginine, aspartic acid, glutamic acid or serine. When $L^1$ comprises a PEG moiety, it preferably comprises units derived from oligomerisation of the monodisperse PEG-like structures of Formulae Bio1 or Bio2:

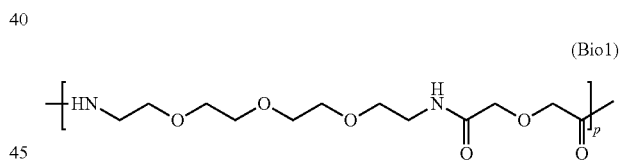

17-amino-5-oxo-6-aza-3,9,12,15-tetraoxaheptadecanoic acid of Formula Bio1 wherein p is an integer from 1 to 10. Alternatively, a PEG-like structure based on a propionic acid derivative of Formula Bio2 can be used:

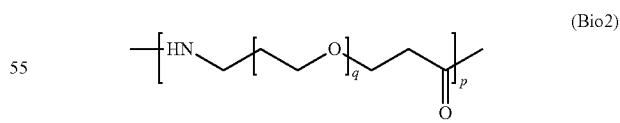

where p is as defined for Formula Bio1 and q is an integer from 3 to 15.

In Formula Bio2, p is preferably 1 or 2, and q is preferably 5 to 12.

When the linker group does not comprise PEG or a peptide chain, preferred $L^1$ groups have a backbone chain of linked atoms which make up the -$(A)_m$- moiety of 2 to 10 atoms, most preferably 2 to 5 atoms, with 2 or 3 atoms being especially preferred.

BTM peptides which are not commercially available can be synthesised by solid phase peptide synthesis as described in P. Lloyd-Williams, F. Albericio and E. Girald; *Chemical Approaches to the Synthesis of Peptides and Proteins*, CRC Press, 1997.

The method of the first aspect preferably further comprises preparing the functionalised BTM of Formula (Ia) or (Ib) by:

(i) provision of a precursor of Formula (IIIa) or (IIIb):

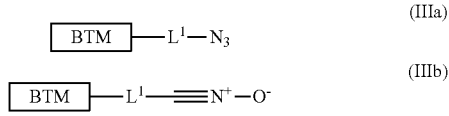

(ii) reaction of said precursor of Formula (IIIa) or (IIIb) with a compound of Formula (IV):

in the presence of a click cycloaddition catalyst, to give the functionalised BTM of Formula (Ia) or (Ib) respectively via click cycloaddition.

The term "click cycloaddition" has its conventional meaning in the field of click chemistry, as described by Lahann [*Click Chemistry for Biotechnology and Materials Science*, John Wiley & Sons (2009)].

By the term "click cycloaddition catalyst" is meant a catalyst known to catalyse the click (alkyne plus azide) or click (alkyne plus isonitrile oxide) cycloaddition reaction. Suitable such catalysts are known in the art for use in click cycloaddition reactions. Preferred such catalysts include Cu(I), and are described below. Further details of suitable catalysts are described by Wu and Fokin [Aldrichim. Acta, 40(1), 7-17 (2007)] and Meldal and Tornoe [Chem. Rev., 108, 2952-3015 (2008)].

In the method of the first aspect, the compound of Formula (IV) may optionally be generated in situ by deprotection of a compound of Formula (IVa):

wherein $M^1$ is an alkyne-protecting group. It is, however, preferred to use the compound of Formula (IV) directly, since that avoids the need for additional protection and deprotection steps and the terminal alkyne of Formula (IV) is stable enough to be used as is.

Preferred aspects of Q in Formula (IVa), are as described for Formulae (Ia) and (Ib).

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Suitable alkyne protecting groups are described in 'Protective Groups in Organic Synthesis', Theodora W. Greene and Peter G. M. Wuts, Chapter 8, pages 927-933, 4$^{th}$ edition (John Wiley & Sons, 2007), and include: an trialkylsilyl group where each alkyl group is independently $C_{1-4}$ alkyl; an aryldialkylsilyl group where the aryl group is preferably benzyl or biphenyl and the alkyl groups are each independently $C_{1-4}$ alkyl; hydroxymethyl or 2-(2-hydroxypropyl). A preferred such alkyne protecting group is trimethylsilyl. The protected iodoalkynes of Formula (IVa) allow the desired alkyne of Formula (IV) to be generated in a controlled manner in situ so that the efficiency of the reaction with the azide derivative of Formula (IIIa) or isonitrile oxide of Formula (IIIb) is maximised.

The method of the first aspect is preferably carried out in an aseptic manner, such that the product of Formula (IIa) or (IIb) is obtained as a radiopharmaceutical composition. Thus, the method is carried out under aseptic manufacture conditions to give the desired sterile, non-pyrogenic radiopharmaceutical product. It is preferred therefore that the key components, especially any parts of the apparatus which come into contact with the product of Formula (IIa) or (IIb) (e.g. vials and transfer tubing) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise the non-radioactive components in advance, so that the minimum number of manipulations need to be carried out on the radioiodinated radiopharmaceutical product. As a precaution, however, it is preferred to include at least a final sterile filtration step.

The compounds of Formula (Ia) or (Ib), and optionally (IIIa) or (IIIb) and (IV), plus click cycloaddition catalyst and other such reagents and solvents are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour. The reaction vessel is suitably chosen from such containers, and preferred embodiments thereof. The reaction vessel is preferably made of a biocompatible plastic (eg. PEEK).

When the radioiodinated BTM product is used as a pharmaceutical composition, the method of the first aspect is preferably carried out using an automated synthesizer apparatus. By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical product is desired. They are commercially available from a range of suppliers [Satyamurthy et al, above], including: GE Healthcare; CTI Inc; Ion Beam Applications S. A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a cassette.

By the term "cassette" is meant a piece of apparatus designed to fit removably and interchangeably onto an automated synthesizer apparatus (as defined below), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (eg. solid phase extraction, SPE). The cassette always comprises a reaction vessel. Such reaction vessels are preferably 1 to 10 cm$^3$, most preferably 2 to 5 cm$^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes of the present invention are designed to be suitable for radiopharmaceutical manufacture and are therefore manufactured from materials which are of pharmaceutical grade and ideally also are resistant to radiolysis.

Preferred automated synthesizers of the present invention are those comprising a disposable or single use cassette which comprises all the reagents, reaction vessels and apparatus necessary to carry out the preparation of a given batch of radioiodinated radiopharmaceutical. The cassette means that the automated synthesizer has the flexibility to be capable of making a variety of different radioiodine-labelled radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

The radioiodination reaction of step (ii) of the first aspect may be effected in a suitable solvent, for example acetonitrile, a $C_{1-4}$ alkylalcohol, dimethylformamide, tetrahydrofuran (THF), or dimethylsulfoxide, or mixtures thereof, or aqueous mixtures thereof, or in water. Aqueous buffers can also be used. The pH will depend on the oxidant used, and will typically be pH 0 to 1 when eg. hydrogen peroxide/aqueous acid is used, or in the range pH 6-8 when iodogen or iodogen tubes are used. The radioiodination reaction temperature is preferably 10 to 60° C., more preferably at 15 to 50° C., most preferably at ambient temperature (typically 15-37° C.). Organic solvents such as acetonitrile or THF and/or the use of more elevated temperature may conveniently be used to solubilise functionalised BTMs which are poorly soluble in water.

When the BTM comprises a tyrosine residue, there may be some competing radioiodination at the tyrosine residue in addition to the Q group of Formulae (Ia) or (Ib). This is, however, expected to be a minor reaction since the kinetics of reaction at the Q group will be rapid.

When Q is $R^a{}_3Sn$—, the radioiodination reaction of step (ii) of the first aspect is carried out as described by Bolton [J. Lab. Comp. Radiopharm., 45, 485-528 (2002)] and Eersels et al [J. Lab. Comp. Radiopharm., 48, 241-257 (2005)].

When Q is $KF_3B$—, the radioiodination reaction of step (ii) of the first aspect can be carried out as described by Kabalka et al [J. Lab. Comp. Radiopharm., 48, 359-362 (2005)], who use peracetic acid as the oxidising agent.

The functionalised BTM of Formula (Ia) or (Ib) is non-radioactive. Such functionalised BTMs are preferably obtained via click cycloaddition from the precursors of Formula (IIIa) or (IIIb), as described for the preferred embodiment (above).

The click cycloaddition may optionally be carried out in the presence of an organic base, as is described by Meldal and Tornoe [Chem. Rev. 108 (2008) 2952, Table 1 (2008)].

A preferred click cycloaddition catalyst comprises Cu(I). The Cu(I) catalyst is present in an amount sufficient for the reaction to progress, typically either in a catalytic amount or in excess, such as 0.02 to 1.5 molar equivalents relative to the compound of Formula (Ia) or (Ib). Suitable Cu(I) catalysts include Cu(I) salts such as CuI or [Cu(NCCH$_3$)$_4$][PF$_6$], but advantageously Cu(II) salts such as copper (II) sulphate may be used in the presence of a reducing agent to generate Cu(I) in situ. Suitable reducing agents include: ascorbic acid or a salt thereof for example sodium ascorbate, hydroquinone, metallic copper, glutathione, cysteine, $Fe^{2+}$, or $Co^{2+}$. Cu(I) is also intrinsically present on the surface of elemental copper particles, thus elemental copper, for example in the form of powder or granules may also be used as catalyst. Elemental copper, with a controlled particle size is a preferred source of the Cu(I) catalyst. A more preferred such catalyst is elemental copper as copper powder, having a particle size in the range 0.001 to 1 mm, preferably 0.1 mm to 0.7 mm, more preferably around 0.4 mm. Alternatively, coiled copper wire can be used with a diameter in the range of 0.01 to 1.0 mm, preferably 0.05 to 0.5 mm, and more preferably with a diameter of 0.1 mm. The Cu(I) catalyst may optionally be used in the presence of bathophenanthroline, which is used to stabilise Cu(I) in click chemistry.

The non-radioactive precursor compounds of Formula (IIIa) and (IIIb), wherein the BTM is a peptide or protein may be prepared by standard methods of peptide synthesis, for example, solid-phase peptide synthesis, for example, as described in Atherton, E. and Sheppard, R. C.; *Solid Phase Synthesis*; IRL Press: Oxford, (1989).

The preparation of the compound of Formula (IIIa) or (IIIb) may be achieved by reaction of the N- or C-terminus of the peptide or with some other functional group contained within the peptide sequence, modification of which does not affect the binding characteristics of the vector. The azide group is preferably introduced by formation of a stable amide bond, for example formed by reaction of a peptide amine function with an activated acid or alternatively reaction of a peptide acid function with an amine function and introduced either during or following the peptide synthesis. Methods for incorporation of an azide group into vectors such as cells, viruses, bacteria may be found in H. C. Kolb and K. B. Sharpless, Drug Discovery Today, Vol 8 (24), December 2003 and the references therein. Suitable bifunctional intermediates useful for incorporation of the azide group in a compound of Formula (IIIa) include:

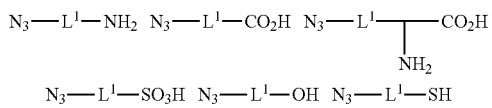

where $L^1$ and preferred embodiments thereof are as defined above. In the above formulae, $L^1$ is suitably present. In the azide-functionalised amino acid, however, the azide functional group may optionally be attached directly to the side chain of the amino acid without any linker group.

Further approaches to functionalising BTMs with azide groups are described by Nwe et al [Cancer Biother. Radiopharm., 24(3), 289-302 (2009)]. Li et al provide the synthesis of a compound of the type $N_3$-$L^1$-$CO_2H$, where $L^1$ is —$(CH_2)_4$— and its use to conjugate to amine-containing BTMs [Bioconj. Chem., 18(6), 1987-1994 (2007)]. Hausner et al describe related methodology for $N_3$-$L^1$-$CO_2H$, where $L^1$ is —$(CH_2)_2$— [J. Med. Chem., 51(19), 5901-5904 (2008)]. De Graaf et al [Bioconj. Chem., 20(7), 1281-1295 (2009)] describe non-natural amino acids having azide side chains and their site-specific incorporation in peptides or proteins for subsequent click conjugation.

The nitrile oxides of Formula (IIIb) can be obtained by the methods described by Ku et al [Org. Lett., 3(26), 4185-4187 (2001)], and references therein. Thus, they are typically generated in situ by treatment of an alpha-halo aldoxime with an organic base such as triethylamine. A preferred method of generation, as well as conditions for the subsequent click cyclisation to the desired isoxazole are described by Hansen et al [J. Org. Chem., 70(19), 7761-7764 (2005)]. Hansen et al generate the desired alpha-halo aldoxime in situ by reaction of the corresponding aldehyde with chloramine-T trihydrate, and then dechlorinating this with sodium hydroxide. The corresponding aldoxime is prepared by reacting the corresponding aldehyde with hydroxylamine hydrochloride at pH 9-10. See also K. B. G. Torsell "Nitrile Oxides, Nitrones and Nitronates in Organic Synthesis" [VCH, New York (1988)]. This nitrile oxide preparative chemistry requires the use of a strong oxidizing agent and a strong base, and is therefore less compatible with base-sensitive and/or oxidation-sensitive BTM.

Compounds of Formula (IV), where Q is $R^a{}_3Sn$— are commercially available from Sigma-Aldrich and other suppliers. Thus, the trialkyltin compounds $Bu_3Sn$—≡—H and $Bu_3Sn$—≡—$SiMe_3$ are commercially available from Sigma-Aldrich. Other organotin intermediates are described by Ali et al [Synthesis, 423-445 (1996)]. Compounds of Formula (IV), where Q is $KF_3B$— can be obtained from the corresponding alkyne as described by Kabalka et al [J. Lab. Comp. Radiopharm., 48, 359-362 (2005) and, J. Lab. Comp. Radiopharm., 49, 11-15 (2006)]. The potassium trifluoroborate precursors are stated to be crystalline solids, which are stable to both air and water.

Compounds of Formula (IVa) can be obtained and deprotected as described in 'Protective Groups in Organic Synthesis', Theodora W. Greene and Peter G. M. Wuts, Chapter 8, pages 927-933, 4$^{th}$ edition, John Wiley & Sons, (2007).

The present invention provides a more chemoselective approach to radioiodination. The radioiodination reaction occurs at a predetermined site in the BTM, with favourable radioiodination reaction kinetics, such that reaction at the Q group is strongly favoured over other possible sites on the BTM. Additionally, both alkyne and azide functionalities are stable under most reaction conditions and are unreactive with most common peptide functionalities—thus minimising the protection and deprotection steps required during the synthesis. Furthermore, the triazole and isoxazole rings do not hydrolyse and are highly stable to oxidation and reduction, meaning that the labelled BTM has high in vivo stability. The triazole ring is also comparable to an amide in size and polarity such that the labelled peptides or proteins are good mimics for their natural counterparts—the triazole ring in particular is a known amide mimetic group or bioisostere. The triazole and isoxazole rings of the products of Formula (IIa) and (IIb) of the present invention are not, however, expected to be recognized by thyroid deiodination enzymes known to metabolise iodo-tyrosine more rapidly than iodobenzene, and are thus expected to be sufficiently stable in vivo for radiopharmaceutical imaging and/or radiotherapy.

In a second aspect, the present invention provides a functionalised biological targeting molecule of Formula (Ia) or (Ib):

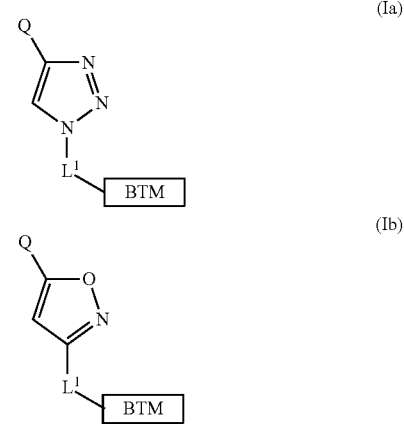

where Q, $L^1$ and BTM and preferred aspects thereof are as described for the first aspect (above).

Preferably, the compound of the second aspect is of Formula (Ia). The functionalised biological targeting molecule of the second aspect is preferably provided in sterile, apyrogenic form. A preferred such sterile form is a lyophilised solid. The sterile form is preferably a pharmaceutical composition comprising said functionalised biological targeting molecule together with a biocompatible carrier medium.

The "biocompatible carrier medium" comprises one or more pharmaceutically acceptable adjuvants, excipients or diluents. It is preferably a fluid, especially a liquid, in which the compound of Formula (Ia) or (Ib) is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

In a third aspect, the present invention provides the use of the functionalised biological targeting molecule of the second aspect in the manufacture of the radioiodinated biological targeting moiety of Formula (IIa) or (IIb) as defined in the first aspect.

Preferred aspects of the functionalised biological targeting molecule and the radioiodinated biological targeting moiety in the third aspect, are as described in the first and second aspects respectively.

In a fourth aspect, the present invention provides the use of the compound of Formula (IV) as defined in the first aspect in the manufacture of the radioiodinated biological targeting moiety of Formula (IIa) or (IIb) as defined in the first aspect.

Preferred aspects of the compound of Formula (IV) and the radioiodinated biological targeting moiety in the fourth aspect, are as described in the first aspect. Preferably, the compound of Formula (IV) is used.

In a fifth aspect, the present invention provides the use of an automated synthesizer apparatus to carry out the method of the first aspect.

The automated synthesizer apparatus and preferred embodiments thereof in the fifth aspect are as described in the first aspect (above).

The invention is illustrated by the following Examples. Example 1 provides the preparation of a model triazole-functionalised tributyltin derivative using the click cycloaddition reaction. Examples 2 and 3 provide the radioiodination of the tributyltin-triazole derivative using two different oxidants. Example 4 provides the preparation of a model isoxazole-functionalised tributyltin derivative using the click cycloaddition reaction. Examples 5 and 6 provide the radioiodination of the tributyltin-isoxazole derivative using two different oxidants.

Abbreviations Used in the Examples.
HPLC: high performance liquid chromatography,
PAA: peracetic acid,
THF: tetrahydrofuran.

EXAMPLE 1

Preparation of 1-Phenyl-4-(tributylstannyl)-1H[1,2,3]triazole (Prophetic example)

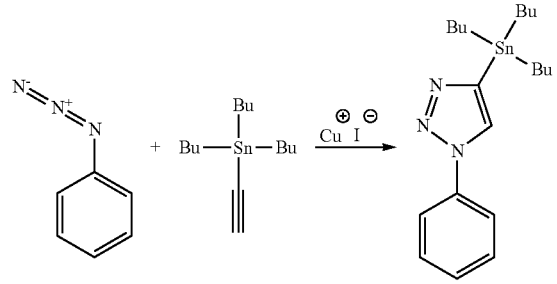

Phenylazide can be obtained from Pfaltz & Bauer, Inc., or can be synthesized by the method described in J. Biochem., 179, 397-405 (1979). A solution of tributylethynyl stannane (Sigma Aldrich; 400 mg, 1.27 mmol) in THF (4 ml) is treated with phenylazide (169 mg, 1.27 mmol), copper (I) iodide (90 mg, 0.47 mmol), and triethylamine (256 mg, 2.54 mmol) at room temperature over 48 h. The reaction is then filtered through celite to remove copper (I) iodide and chromatographed on silica in a gradient of 5-20% ethyl acetate in petrol. The second fraction is collected and concentrated in vacuo to give the 1-phenyl-4-(tributylstannyl)-1H[1,2,3]triazole as a colourless oil.

EXAMPLE 2

Preparation of $[^{123}I]$-1-phenyl-4-iodo-1H[1,2,3]triazole Using Peracetic Acid as the Oxidant (Prophetic example)

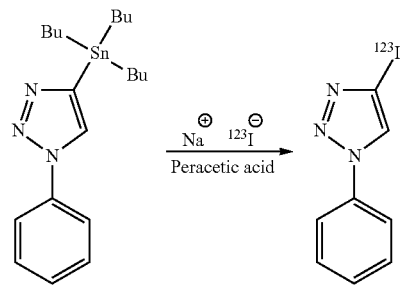

To sodium $[^{123}I]$ iodide, received in 5-20 μL 0.05M sodium hydroxide is added ammonium acetate buffer (100 μL pH 4.0, 0.2M), sodium $[^{127}I]$ iodide (10 μL 15 mg/10 ml 0.01M sodium hydroxide, $1 \times 10^{-8}$ moles), peracetic acid (PAA) solution (10 μL 0.01M solution, $1 \times 10^{-8}$ moles) and finally, 1 phenyl-4-tributylstannyl-1H[1,2,3]triazole (Example 1; 23 μg, $1 \times 10^{-7}$ moles). The reaction mixture is incubated at room temperature for 15 minutes prior to purification by HPLC.

EXAMPLE 3

Preparation of $[^{123}I]$-1-Phenyl-4-iodo-1H[1,2,3]triazole Using an Iodogen Tube as the Oxidant (Prophetic example)

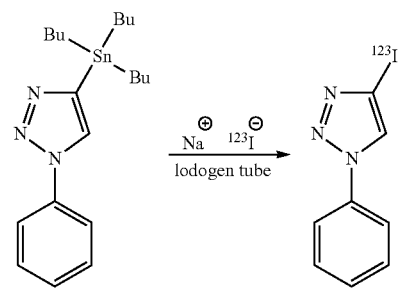

To an iodogen tube (Thermo Scientific Pierce Protein Research Products), pre-wet with 1 ml pH 7.4, 25 mM sodium phosphate buffer and subsequently decanted is added sodium phosphate buffer (100 μL, pH7.4, 25 mM), and sodium $[^{123}I]$ iodide received in 5-20 μL 0.05M sodium hydroxide. The reaction is allowed to stand at room temperature for 6 minutes with agitation prior to the addition of 1 phenyl-4-tributylstannyl-1H[1,2,3]triazole (Example 1; 23 μg, 1×10⁻⁷ moles). The reaction mixture is incubated at room temperature for 15 minutes prior to purification by HPLC.

EXAMPLE 4

Preparation of 3-Phenyl-5-(tributylstannyl)isoxazole (Prophetic example)

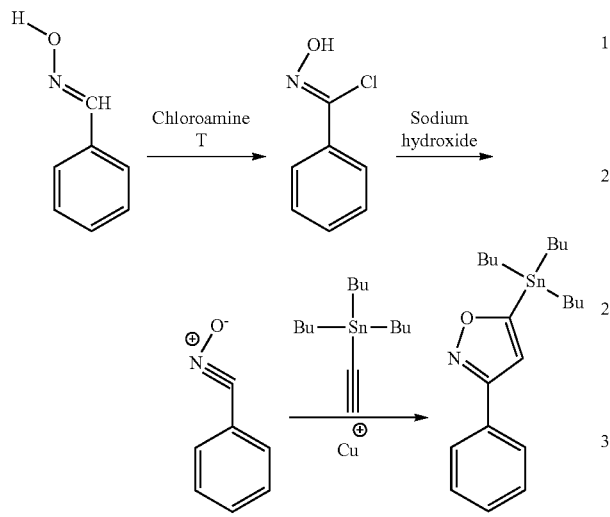

(E)-benzaldehyde oxime (Sigma Aldrich; 3.3 g, 20 mmol) in tent butanol and water (1:1) 80 ml, is treated with chloramine T trihydrate (Sigma Aldrich; 5.9 g, 21 mmol) in small, portions over 5 min. The reaction is then treated with copper sulfate pentahydrate (0.15 g, 0.6 mmol) and copper turnings ~50 mg and tributylethynylstannane (6.3 g, 20 mmol). The reaction is then adjusted to pH 6 with sodium hydroxide solution and stirred for 6 h. The reaction mixture is treated with dilute ammonium hydroxide solution to remove all copper salts. The product is collected by filtration, redissolved in ethyl acetate and filtered through a short plug of silica gel. The filtrate is concentrated in vacuum to give 3-phenyl-5-(tributylstannyl) isoxazole.

EXAMPLE 5

Preparation of [$^{123}$I]-3-phenyl-5-iodo isoxazole using peracetic acid as an oxidant (Prophetic example)

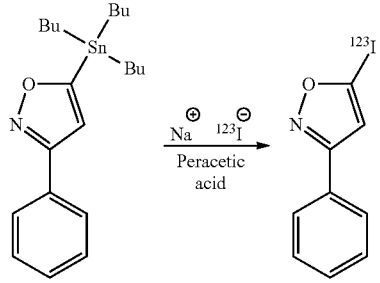

To sodium [$^{123}$I] iodide, received in 5-20 μL 0.05M sodium hydroxide is added ammonium acetate buffer (100 μL pH4.0, 0.2M), sodium [$^{127}$I] iodide (10 μL 15 mg/10 ml 0.01M sodium hydroxide, 1×10⁻⁸ moles), peracetic acid (PAA) solution (10 μL 0.01M solution, 1×10⁻⁸ moles) and finally, [$^{123}$I]-3-phenyl-5-tributylstannyl-isoxazole (Example 4; 23 μg, 1×10⁻⁷ moles). The reaction mixture is incubated at room temperature for 15 minutes prior to purification by HPLC.

EXAMPLE 6

Preparation of [$^{123}$I]-3-phenyl-5-iodo isoxazole using Iodogen Tube as an Oxidant (Prophetic example)

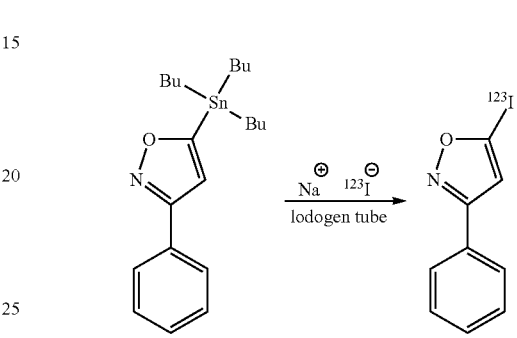

To an iodogen tube, pre-wet with 1 ml pH 7.4, 25 mM sodium phosphate buffer and subsequently decanted is added sodium phosphate buffer (100 μL, pH7.4, 25 mM), and sodium [$^{123}$I] iodide received in 5-20 μL 0.05M sodium hydroxide. The reaction is allowed to stand at room temperature for 6 minutes with agitation prior to the addition of [$^{123}$I]-3-phenyl-5-tributylstannyl-isoxazole (Example 4; 23 μg, 1×10⁻⁷ moles). The reaction mixture is incubated at room temperature for 15 minutes prior to purification by HPLC.

The invention claimed is:

1. A method of radioiodination of a biological targeting moiety, said method comprising:
   (i) provision of a functionalised BTM of Formula (Ia) or (Ib):

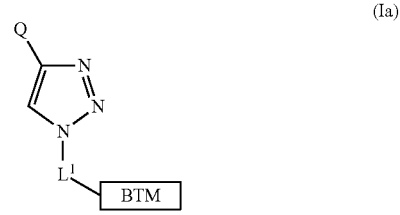

(Ia)

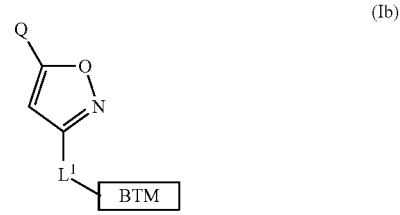

(Ib)

(ii) reaction of the functionalised BTM of either Formula (Ia) or (Ib) with radioactive iodide ion in the presence of an oxidising agent, to give the desired radioiodinated product as a conjugate of Formula (IIa) or (IIb) respectively;

(IIa)

[Structure: triazole with I* at 4-position, L¹-BTM at N1]

(IIb)

[Structure: isoxazole with I* at 5-position, L¹-BTM at 3-position]

wherein:

BTM is the biological targeting moiety;

L¹ is a linker group which may be present or absent;

Q is $R^a{}_3Sn-$ or $KF_3B-$, where each $R^a$ is independently $C_{1-4}$ alkyl;

I* is a radioisotope of iodine.

2. The method according to claim 1, where I* is chosen from $^{123}I$, $^{124}I$ or $^{131}I$.

3. The method according to claim 1, where BTM is a single amino acid, a 3-100 mer peptide, an enzyme substrate, an enzyme antagonist an enzyme agonist, an enzyme inhibitor or a receptor-binding compound.

4. The method according to claim 1, further comprises preparing the functionalised BTM of Formula (Ia) or (Ib) by:

(i) provision of a precursor of Formula (IIIa) or (IIIb):

BTM—L¹—N₃ (IIIa)

BTM—L¹—≡N⁺—O⁻ (IIIb)

(ii) reaction of said precursor with a compound of Formula (IV):

Q—≡—H (IV)

in the presence of a click cycloaddition catalyst, to give the functionalised BTM of Formula (Ia) or (Ib) respectively via click cycloaddition.

5. The method according to claim 4, where the click cycloaddition catalyst comprises Cu(I).

6. The method according to claim 5, where the Cu(I) catalyst comprises elemental copper.

7. The method of claim 1, where the functionalised biological targeting molecule is of Formula (Ia), and the radio-iodinated product is the conjugate of Formula (IIa).

8. The method of claim 1, is carried out in an aseptic manner, such that the product of Formula (IIa) or (IIb) is obtained as a radiopharmaceutical composition.

9. A functionalised biological targeting molecule of Formula (Ia) or (Ib):

(Ia)

[Structure: triazole with Q at 4-position, L¹-BTM at N1]

(Ib)

[Structure: isoxazole with Q at 5-position, L¹-BTM at 3-position]

where Q and L¹ are as defined in claim 1, and BTM is as defined in claim 1.

10. The functionalised biological targeting molecule of claim 9, is provided in sterile, apyrogenic form.

11. The functionalised biological targeting molecule of claim 10, where the sterile form is a pharmaceutical composition comprising said functionalised biological targeting molecule together with a biocompatible carrier medium.

* * * * *